United States Patent [19]

DeLavarenne et al.

[11] 4,365,100
[45] Dec. 21, 1982

[54] PROCESS FOR THE PREPARATION OF 1,2,3,4-TETRAHYDRO-9,10-ANTHRACENE-DIOL

[75] Inventors: Serge Y. DeLavarenne, Francheville-le-Haut; Pierre Tellier, Sainte-Foy-les-Lyon, both of France

[73] Assignee: PCUK - Produits Chimiques Ugine Kuhlmann, Courbevoie, France

[21] Appl. No.: 52,282

[22] Filed: Jun. 26, 1979

[30] Foreign Application Priority Data

Jun. 29, 1978 [FR] France ............................. 78 19465

[51] Int. Cl.$^3$ ........................................... C07C 39/17
[52] U.S. Cl. .................................................. 568/733
[58] Field of Search ................. 568/719, 733; 560/139

[56] References Cited

U.S. PATENT DOCUMENTS 1,890,040 12/1932 Luttringhaus et al. ......... 260/369 R
2,495,229 1/1950 Dawsey et al. ..................... 260/690

OTHER PUBLICATIONS

Roberts, John D., *Basic Principles of Organic Chemistry*, (1966), (W. A. Benjamin, Publ.), p. 476.
Skita, A. *Berichte der deutschen chemischen Gesellschaft*, vol. 58, (1925), pp. 2685–2689.
Skita, A. *Berichte der deutschen chemischen Gesellschaft*, vol. 60, (1927), pp. 2522–2527.

*Primary Examiner*—Natalie Trousof
*Assistant Examiner*—L. Hendriksen
*Attorney, Agent, or Firm*—Beveridge, DeGrandi & Kline

[57] ABSTRACT

A process for the preparation of 1,2,3,4-tetrahydro-9,10-anthracene-diol, in which catalytic hydrogenation of 1,4,4a,9a-tetrahydro-anthraquinone is carried out in the liquid phase to give 1,2,3,4,4a,9a-hexahydro-9,10-anthracene-dione followed by isomerization of the latter in the presence of an acid to give 1,2,3,4-tetrahydro-9,10-anthracene-diol.

10 Claims, No Drawings

PROCESS FOR THE PREPARATION OF 1,2,3,4-TETRAHYDRO-9,10-ANTHRACENE-DIOL

The present invention relates to a new process for the preparation of 1,2,3,4-tetrahydro-9,10-anthracene-diol.

It is known that 1,2,3,4-tetrahydro-9,10-anthracene-diol can be obtained by catalytic hydrogenation of anthraquinone (Skita—Ber. 1925 58—2685-97). However, this very slight selective reaction does not enable good yields of 1,2,3,4-tetrahydro-9,10-anthracene-diol to be obtained.

Applicants have now found that it is possible to obtain this product with very good yields. In the process according to the invention, 1,4,4a,9a-tetrahydro-anthraquinone is catalytically hydrogenated to 1,2,3,4,4a,9a-hexahydro-9,10-anthracene-dione and the latter is isomerized in acid medium to 1,2,3,4-tetrahydro-9,10-anthracene-diol. These two reactions may be carried out successively or simultaneously. In the latter case, the hydrogenation is effected in the presence of an acid.

The process of the invention has multiple advantages. It makes use of an inexpensive starting material, the 1,4,4a,9a-tetrahydro-anthraquinone, easily accessible by diene synthesis from naphthoquinone and butadiene. The hydrogenation may be effected in the presence of catalysts other than those based on precious metals: catalysts based on nickel, for example, are perfectly suitable. Finally, the conversion of the 1,4,4a,9a-tetrahydro-anthraquinone into 1,2,3,4-tetrahydro-anthracene-diol is made with a very good yield.

The hydrogenation of the 1,4,4a,9a-tetrahydro-anthraquinone according to the present invention leads in the majority of cases to a mixture of 1,2,3,4,4a,9a-hexahydro-9,10-anthracene-dione and 1,2,3,4-tetrahydro-9,10-anthracene-diol in variable proportions according to the conditions of the reaction. It is possible to separate these two compounds by known means, especially by making use of their difference in solubility, and of carrying out the isomerization only on the 1,2,3,4,4a,9a-hexahydro-9,10-anthracene-dione thus isolated. It is also possible, and this is one of the great advantages of the present invention, to subject the mixture of the two compounds to the isomerization treatment. Another possibility is to effect the hydrogenation in a solvent which simultaneously entrains the isomerization of 1,2,3,4,4a,9a-hexahydro-9,10-anthracene-dione into 1,2,3,4-tetrahydro-9,10-anthracene-diol so as to obtain directly the latter in a single stage.

According to the process of the invention, the hydrogenation is effected in the liquid phase, the 1,4,4a,9a-tetrahydro-anthraquinone being in solution in one of the solvents normally used for hydrogenations. As examples of such solvents may be mentioned aliphatic, cycloaliphatic or aromatic hydrocarbons, ethers, tetrahydrofuran, dioxan, and alcohols. Generally speaking, all solvents not containing a hydrogenable functional group under the conditions of the reaction may be used.

The catalyst is selected from those generally used in hydrogenation. Examples of these include those based on nickel, such as Raney nickel, and those based on precious metals such as palladium or platinum.

As stated above, the solvents and catalysts used are those generally used in hydrogenations. Such hydrogenations, the solvents and catalysts used therefore are described, for example, in M. Freifelder—Practical Catalytic Hydrogenation—Wiley Interscience—New York—1971.

The hydrogenation reaction may be carried out in a large range of temperatures going from 20° to 200° C. However, it is preferred to operate between 60° and 130° C.

The hydrogenation may be carried out at atmospheric pressure but it is then slow. It is therefore preferable to operate under pressure. There is no upper limit to the hydrogenation pressure, which is preferably chosen between 10 and 50 bars. The admission of hydrogen is maintained until the theoretical quantity of hydrogen corresponding to the formation of the hexahydroanthracene-dione has been absorbed.

The concentration of 1,4,4a,9a-tetrahydro-anthraquinone in the reaction medium can also vary within wide limits. There is no lower limit to this concentration, but for reasons of productivity it is preferably greater than 10% by weight. For practical reasons, it is less than 50%. The preferred concentration is from 15 to 40%.

According to the process of the invention, the isomerization of 1,2,3,4,4a,9a-hexahydro-9,10-anthracene-dione is effected by a treatment in acid medium in the absence of oxygen. The acid used to carry out the isomerization may be a mineral or an organic acid. Examples of mineral acids are sulfuric, hydrochloric and phosphoric acids. The organic acids consist of carboxylic acids, among which may be mentioned, for example, formic, acetic, propionic and butyric acids.

The isomerization may be carried out at temperatures as low as 20° C., but it is then slow. For this reason it is preferred to operate at a higher temperature preferably chosen from between 50° and 200° C. If it is wished to effect the hydrogenation and the isomerization in a single stage, the hydrogenation of the 1,4,4a,9a-tetrahydro-anthraquinone is effected in the presence of a mineral or organic acid such as those mentioned above.

The examples which follow illustrate the present invention without limiting it thereto. All proportions are by weight unless otherwise stated.

EXAMPLE 1

100 ml of toluene, 21.2 g of 1,4,4a,9a-tetrahydroanthraquinone and 0.2 g of a catalyst based on palladium deposited on charcoal, containing 5% of palladium, are introduced into a stainless steel autoclave provided with devices for heating and agitation. The mixture is heated to 100° C. and hydrogen is introduced under a pressure of 30 bars. The reaction is continued for 4 hours while maintaining the pressure at between 20 and 30 bars. After cooling, there are separated by filtration 7 g of a first fraction consisting of 1,2,3,4-tetrahydro-9,10-anthracene-diol melting at 206°-208° C., characterized by its IR and NMR spectra. By concentration of the filtrate, 14 g of a second fraction are obtained, which consists of a product melting at 86°-88° C. The IR, NMR and mass spectra show that it is practically pure 1,2,3,4,4a,9a-hexahydro-9,10-anthracene-dione. This second fraction is dissolved in 42 g of acetic acid and the mixture is refluxed under nitrogen for 4 hours. After cooling to 0° C., the crystals which are formed are filtered off, washed with water and dried under reduced pressure. 12.7 Grams of a crystalline product melting at 210°-212° C. are thus obtained, the IR spectrum of which is the same as that of the first fraction, and corresponds to 1,2,3,4-tetrahydro-9,10-anthracene-diol. The total yield is 92% without taking into account the fraction of product remaining in solution in the acetic acid.

EXAMPLE 2

Hydrogenation of the 1,4,4a,9a-tetrahydro-anthraquinone is effected by operating as in Example 1 but replacing the palladium catalyst by 2 g of a nickel catalyst obtained by the action of caustic soda on 4 g of a nickel-aluminum alloy containing 50% of nickel, and carrying out the reaction at 60° C. for 5½ hours under a pressure of hydrogen of 30 bars. The catalyst is separated and the solvent is evaporated under reduced pressure. 20.2 g of a residue are obtained which is treated with 60 g of acetic acid as in Example 1. Finally 18.4 g of 1,2,3,4-tetrahydro-9,10-anthracene-diol are obtained the IR spectrum of which is the same as that of the product obtained in Example 1. The yield is 86% without taking into account the fraction of product remaining in solution in the acetic acid.

EXAMPLE 3

300 ml of acetic acid, 64 g of 1,4,4a,9a-tetrahydroanthraquinone and 0.6 g of a catalyst containing 5% of palladium deposited on charcoal are introduced into an autoclave. The charge is heated to 100° C. and hydrogen is introduced under a pressure of 30 bars. The reaction is continued for 4 hours while maintaining the pressure at between 20 and 30 bars. After cooling, the precipitate obtained is separated by filtration, washed with water and dried. 56 Grams of 1,2,3,4-tetrahydro-9,10-anthracene-diol (melting point 210°–212° C.) are obtained. The yield is 86.7% without taking into account the fraction of product remaining in solution in the acetic acid.

What is claimed is:

1. A process for the preparation of 1,2,3,4-tetrahydro-9,10-anthracene-diol from 1,4,4a,9a-tetrahydroanthraquinone which comprises effecting a catalytic hydrogenation in the liquid phase of 1,4,4a,9a-tetrahydroanthraquinone to convert it into 1,2,3,4,4a,9a-hexahydro-9,10-anthracene-dione or into a mixture of 1,2,3,4-tetrahydro-9,10-anthracene-diol and 1,2,3,4,4a,9a-hexahydro-9,10-anthracene dione, and then effecting isomerization of the latter in the presence of an acid to give 1,2,3,4-tetrahydro-9,10-anthracene-diol.

2. A process according to claim 1 in which the 1,2,3,4,4a,9a-hexahydro-9,10-anthracene-dione is separated from the 1,2,3,4-tetrahydro-9,10-anthracene diol and is then subjected to isomerization in the presence of an acid.

3. A process according to claim 1 in which a mixture of 1,2,3,4,4a,9a-hexahydro-9,10-anthracene-dione and 1,2,3,4-tetrahydro-9,10-anthracene-diol is treated with an acid.

4. A process according to claim 1 in which the hydrogenation and isomerization are effected in a single stage, the acid being present in the medium of hydrogenation.

5. A process according to claim 1 in which the catalyst is based on nickel or a precious metal.

6. A process according to claim 1 in which the solvent is an organic solvent free of any hydrogenable functional group.

7. A process according to claim 1, 5 or 6 in which the hydrogenation temperature is between 20° and 200° C., preferably between 60° and 130° C.

8. A process according to claim 7 in which the hydrogenation is effected under pressure, preferably at between 10 and 50 bars.

9. A process according to claim 1, 5 or 6 in which the hydrogenation is effected under pressure, and preferably between 10 and 50 bars.

10. A process according to claim 1, 2, 3 or 4 wherein the acid used for the isomerization is a mineral acid or an organic acid.